(12) United States Patent
Banerji

(10) Patent No.: US 12,128,045 B2
(45) Date of Patent: *Oct. 29, 2024

(54) PLATINUM-RESISTANT CANCER TREATMENT

(71) Applicant: BTG International Limited, London (GB)

(72) Inventor: Udai Banerji, Sutton (GB)

(73) Assignee: BTG International Limited, London (GB)

( * ) Notice: Subject to any disclaimer, the term of this patent is extended or adjusted under 35 U.S.C. 154(b) by 845 days.

This patent is subject to a terminal disclaimer.

(21) Appl. No.: 17/306,052

(22) Filed: May 3, 2021

(65) Prior Publication Data

US 2021/0252001 A1 Aug. 19, 2021

Related U.S. Application Data

(63) Continuation of application No. 16/810,160, filed on Mar. 5, 2020, now Pat. No. 11,026,948, which is a continuation of application No. 16/613,912, filed as application No. PCT/IB2018/053428 on May 16, 2018, now abandoned.

(60) Provisional application No. 62/513,627, filed on Jun. 1, 2017.

(30) Foreign Application Priority Data

May 16, 2017 (GB) .................................... 1707864

(51) Int. Cl.
| | |
|---|---|
| A61K 31/517 | (2006.01) |
| A61K 31/282 | (2006.01) |
| A61K 31/337 | (2006.01) |
| A61K 31/4745 | (2006.01) |
| A61K 31/502 | (2006.01) |
| A61K 31/519 | (2006.01) |
| A61K 31/704 | (2006.01) |
| A61K 31/7048 | (2006.01) |
| A61K 31/7068 | (2006.01) |
| A61K 33/243 | (2019.01) |
| A61K 39/00 | (2006.01) |
| A61K 39/395 | (2006.01) |
| A61K 47/64 | (2017.01) |
| A61K 47/69 | (2017.01) |
| A61P 35/00 | (2006.01) |

(52) U.S. Cl.
CPC .......... *A61K 31/517* (2013.01); *A61K 31/282* (2013.01); *A61K 31/337* (2013.01); *A61K 31/4745* (2013.01); *A61K 31/502* (2013.01); *A61K 31/519* (2013.01); *A61K 31/704* (2013.01); *A61K 31/7048* (2013.01); *A61K 31/7068* (2013.01); *A61K 33/243* (2019.01); *A61K 39/3955* (2013.01); *A61K 47/643* (2017.08); *A61K 47/6929* (2017.08); *A61P 35/00* (2018.01); *A61K 2039/545* (2013.01)

(58) Field of Classification Search
CPC .......................... A61K 31/517; A61K 47/6929
See application file for complete search history.

(56) References Cited

U.S. PATENT DOCUMENTS

| | | | |
|---|---|---|---|
| 7,250,511 B2 | 7/2007 | Bavetsias | |
| 7,297,701 B2 | 11/2007 | Bavetsias | |
| 7,528,141 B2 | 5/2009 | Bavetsias | |
| 8,466,111 B2 | 6/2013 | Jansen | |
| 8,809,526 B2 | 8/2014 | Kerschen | |
| 9,458,188 B2 | 10/2016 | Kerschen | |
| 2013/0345423 A1 | 12/2013 | Kershen | |

FOREIGN PATENT DOCUMENTS

| | | |
|---|---|---|
| EP | 1 420 809 B1 | 5/2004 |
| EP | 1 421 069 B | 5/2004 |
| EP | 1 421 105 B | 5/2004 |
| EP | 2 293 807 B1 | 3/2011 |
| EP | 2 655 398 B1 | 10/2013 |
| WO | WO 2009/115776 A1 | 9/2009 |
| WO | WO 2012/011939 A2 | 1/2012 |
| WO | WO 2012/087888 A2 | 6/2012 |

OTHER PUBLICATIONS

Banerji, Udai et al., An investigator-initiated phase I study of ONX-0801, a first-in-class alpha folate receptor targeted, small molecule thymidylate synthase inhibitor in solid tumors, Journal of Clinical Oncology (2017) (two pages).

Chau, et al., "Abstract 2544: Preclinical pharmacodynamics (PD) of ONX 0801, a folate receptor-a (FRa) and tumor-targeted thymidylate synthase (TS) inhibitor," American Association of Cancer Research, (2011) (four pages).

Cocconi, G. et al., "Open, randomized, multicenter trial of raltitrexed versus fluorouracil plus high-dose leucovorin in patients with advanced colorectal cancer," Journal of Clinical Oncology, vol. 16, No. 9, pp. 2943-2952 (1998).

Gibbs, David D. et al, "BGC 945, a Novel Tumor-Selective Thymidylate Synthase Inhibitor Targeted to a-Folate Receptor-Overexpressing Tumors", Cancer Res., 65(24), pp. 11721-11728 (2005).

(Continued)

*Primary Examiner* — Kamal A Saeed
(74) *Attorney, Agent, or Firm* — FINNEGAN, HENDERSON, FARABOW, GARRETT & DUNNER, LLP

(57) ABSTRACT

A compound of formula I or a pharmaceutically acceptable salt or ester thereof is provided for the treatment of cancer wherein (i) the cancer is one that has the characteristic of being a type prone to being or becoming refractory or resistant to platinum drug based therapy and (ii) the treatment is with a dose of between 1 mg/m$^2$ and 30 mg/m$^2$ of compound per patient body surface area per administration. Method of treatment and novel dosage forms are also provided. Particularly treated are ovarian cancers, particularly those expressing a-folate receptors, including epithelial ovarian, fallopian tube or peritoneal cancer.

25 Claims, 4 Drawing Sheets

(56) References Cited

OTHER PUBLICATIONS

Figure 1:
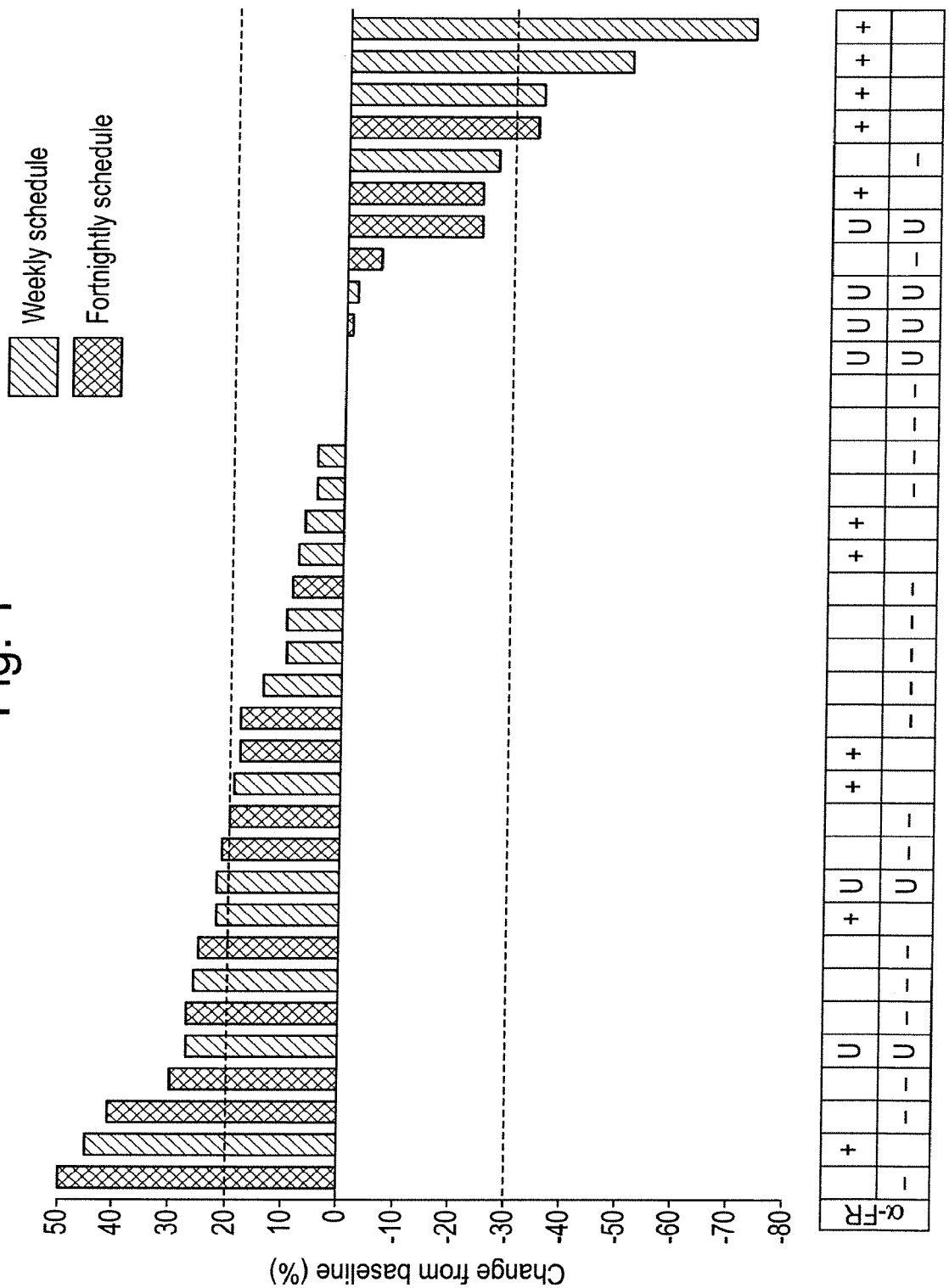

Jackman, Ann L. et al., "Targeting thymidylate synthase by antifolate drugs for the treatment of cancer," Cancer Drug Design and Discovery, pp. 198-226 (2008).

Kurosaki, Akira et al., "Serum folate receptor alpha as a biomarker for ovarian cancer: Implications for diagnosis, prognosis and predicting its local tumor expression," International Journal of Cancer 138, pp. 1994-2002 (2016).

"London Cancer Alliance Clinical Trials Directory Phase I Studies", London Cancer Alliance (2016) (seven pages).

"Phase I Trial of ONX-0801 Once Weekly or Alternate Weekly (ONX-0801 )", Study Details, U.S. National Library of Medicine, https://clinicaltrials.gov, pp. 1-7 (2015).

"Phase I Trial of ONX-0801 Once Weekly or Alternate Weekly (ONX-0801 )" Tabular View, U.S. National Library of Medicine, https://clinicaltrials.gov, pp. 1-7 (2015).

International Search Report for International Application No. PCT/IB2018/053428, Sep. 9, 2018 (three pages).

Written Opinion of the International Search Authority for International Application No. PCT/IB2018/053428 (six pages).

PLATINUM-RESISTANT CANCER TREATMENT

This application is a continuation of application Ser. No. 16/810,160, filed Mar. 5, 2020, which is a continuation of application Ser. No. 16/613,912, filed Nov. 15, 2019, which is a national stage filing under 35 U.S.C. § 371 of International Application No. PCT/IB2018/053428, filed May 16, 2018, which claims priority to British Patent Application No. 1707864.3, filed May 16, 2017, and claims priority to U.S. Provisional Application No. 62/513,627, filed Jun. 1, 2017. The contents of each of these applications are hereby incorporated by reference in their entirety.

The present invention relates to novel treatment for cancer, more particularly for cancers that often show resistance to, or are otherwise refractory to, platinum based therapy. Particular cancers that are to be treated include ovarian, endometrial, mesothelial and non-small cell lung (NSCL), and cancers derived from these. More particularly preferred treatment is provided for ovarian derived cancers such as epithelial ovarian, fallopian tube and peritoneal.

Most particularly the present invention provides novel treatment for such cancers that carry α-folate receptors (FR-α), and especially those showing higher than background non-cancerous tissue levels of α-folate receptors, and particularly those having those FR-α on the surface of their cellular membranes. Cancers suitable for the present treatment also include FR-α expressing breast and lung cancers, particularly triple negative breast cancer.

The α-folate receptor is overexpressed in many carcinomas, particularly those of ovarian origin where it is overexpressed highly and homogeneously in 90% of cases; see *Cancer Res.* 51, 5329-5338, 1991 (Campbell et al., 1991). Furthermore, high α-FR expression has been linked to aggressive, platinum resistant disease and poor prognosis—see *Int. J. Cancer* 74, 193-198, 1997 and *Int. J. Cancer* 79, 121-126, 1998 (both Toffoli et al.). The β-isoform is widely expressed in tumours of epithelial and non-epithelial origin with expression levels being generally low/moderate and high, respectively, reviewed in *Critical Rev. Therap.* in *Drug Carrier Systems* 15, 587-627, 1998 (Reddy and Low).

The present invention particularly advantageously provides a treatment for patients with High-Grade Serous Ovarian Carcinoma (HGSOC), such as in the salvage setting where there is high unmet medical need for products that are able to extend life.

Ovarian cancer is a term for a group of tumours that arise from diverse types of tissue contained in the ovary. The most common type of ovarian cancer arises from epithelial cells on the surface of the ovary, and can often spread to any surface within the abdominal cavity including the fallopian tubes and peritoneal cavity. Fallopian tube cancer and primary peritoneal cancer are histologically equivalent diseases to epithelial ovarian cancer. Ovarian cancer is classified from Stage I to Stage IV. Advanced ovarian cancer falls within Stages III and IV; Stage III denotes disease that is locally advanced and has spread outside the pelvis into the abdominal cavity and Stage IV denotes that distant metastasis to other body organs such as the liver and lungs has occurred.

Epithelial ovarian cancers (EOCs) are the most common cause of death from gynaecological malignancy in the developed world. EOCs comprise a heterogeneous group of neoplasms including serous (68%), clear cell (13%), endometrioid (9%) and mucinous (3%) pathological subtypes. Serous ovarian carcinomas are further divided into low-grade (type I) and high-grade (type II) serous ovarian carcinomas (LGSOC and HGSOC, respectively). Most deaths are attributable to HGSOC which is approximately 20 times more common than LGSOC.

Ovarian cancer may be categorised according to the response to initial platinum chemotherapy as follows:
  platinum-sensitive—disease responds to platinum-based therapy but may relapse after 6 months or more, which can be subdivided into
    fully platinum-sensitive—disease responds to platinum-based therapy but relapses after 12 months or more and
    partially platinum-sensitive—disease responds to platinum-based therapy but relapses between 6 and 12 months; and
  platinum-resistant—disease which relapses within 6 months of completion of platinum-based chemotherapy and
  platinum-refractory—disease does not respond to initial platinum-based chemotherapy.

Although a significant percentage of people have disease that responds to initial chemotherapy, between 55% and 75% of these relapse within 2 years of completing treatment. In addition to these scenarios, some patients are intolerant to treatment with platinum based drugs and thus will also need alternate options to platinum that the regimens of the present invention now provide.

The initial therapeutic approach for HGSOCs is usually surgical tumor debulking followed by chemotherapy. Optimal debulking, with no macroscopic residual disease, is the most important prognostic indicator. However, as HGSOC is asymptomatic in the early stages most patients present with advanced stage disease.

Most HGSOCs (80%) respond well to platinum/taxane therapy initially, with drug resistance emerging during subsequent treatment cycles. However, a minority of HGSOC cases (20%) are refractory to platinum-based chemotherapy from the time of presentation, but the basis for this drug resistance is not known. Disease Stages III and IV, a preferred target population for the present treatment, have a high rate of recurrence.

Patients with optimally debulked (≤1 cm) Stage III ovarian cancer are typically offered intraperitoneal (IP) chemotherapy after front-line surgery. At this time, there is no standardized regimen for IP therapy; however, dosing regimens with drugs such as paclitaxel and cisplatin, or a carboplatin regimen may be used. If the patient cannot tolerate IP delivery then intravenous drug may be given such as paclitaxel and carboplatin or docetaxel plus carboplatin.

Treatment of Stage III and IV disease is usually with chemotherapy; the treatment choice depends on the time elapsed since previous complete response to platinum-containing chemotherapy. Although liposomal doxorubicin is a good first choice, there are many agents with similar efficacy and the final choice depends on individual circumstance and patient and physician preference. Some of the drugs available include Gemcitabine, Topetecan, Paclitaxel, Docetaxel, Etoposide and Nanoparticle albumin-bound paclitaxel. Consideration may also be given to bevacizumab as a single agent or in combination with paclitaxel, pegylated liposomal doxorubicin, or topotecan.

Other possible therapies in drug company pipelines include PARP inhibitors, such as Lynparza (olaparib) and Rubraca (rucaparib) (both labels limited to BRCA mutations) and Zejula (niraparib); and check point inhibitors such as Tecentriq (atezoizumab) and Bavercio (avelumab) for non BRCA mutations. However many key opinion leaders have expressed the belief that such drugs need to be used with more clearly identified populations to be capable of increasing overall response rates. Keytruda (pembrolizumab) has also been found to have some efficacy where high levels of PD-1 are found on T-lymphocytes and tumours.

Several FR-α targeted drugs have been put into clinical trials. The FR-α targeted monoclonal antibody Farletuzumab failed to improve progression free survival (PFS) in patients with platinum-sensitive epithelial ovarian cancer in a 1,100 patient Phase III clinical in combination with paclitaxel and carboplatin. Vintafolide, a conjugate of an α-folate receptor targeting moiety with Vinblastine, has shown some success at improving PFS in combination with docetaxel in folate receptor positive non-small cell lung cancer (NSCLC) and has been trialled together with pegylated liposomal doxorubicin (PLD) in ovarian cancer but the Phase III trial failed to meet the prespecified criteria for PFS to allow continuation of the study. Antibody-drug conjugate IMGN853 (mirvetuximab soravtansine) has also been through Phase I trial in platinum resistant epithelial ovarian cancer with some indication of potential for increasing PFS at a dose of 6 mg/kg every three weeks with PFS of 6.7 months in 39% of patients who had three or less prior lines of therapy.

Despite the possibility that combinations of these agents may prove useful in the platinum resistant setting, there remains a need for treatment of platinum resistant cancers and particularly ovarian cancers such as HGSOC as it accounts for the most ovarian deaths and has shown little improvement in overall survival for decades. Whereas potential blockbuster drugs such as immune checkpoint inhibitors have yielded impressive clinical responses in melanoma and non-small cell lung cancer, possibly due to exceptionally high mutational loads, by contrast HGSOC has intermediate mutational load with lower numbers of neoantigens expected. (Bowtell et al. Nat Rev Cancer 2016 June). Current single agent HGSOC therapies have overall response rates (ORR) of 15-20% and progression free survival (PFS) of only 3 to 4 months.

A further drug class includes the thymidylate synthase (TS) inhibitors CB3717, ZD1694 (raltitrexed), LY231514 Alimta (pemetrexed) and ZD9331 (plevitrexed). All of these TS inhibitors have demonstrable clinical activity in a range of solid tumours (see *Cancer Treatment Reports*, 1986, 70, 1335 and Beale et al., "Tomudex: Clinical Development" in *Antifolate Drugs in Cancer Therapy* (ed. Jackman), Humana Press, Totowa, New Jersey, USA, pp. 177-181, 1999). Side-effects of raltitrexed and ZD9331 are predominantly related to inhibition of TS in gut and bone-marrow.

Raltitrexed and pemetrexed are examples of "classical" TS inhibitors defined by the following properties: the reduced foliate carrier (RFC) is the main transporter into cells; they are excellent substrates for folylpolyglutamate synthase (FPGS) and thus extensively polyglutamated in tissues/tumours to polyglutamates which are effective cytotoxic drug species; and they have fairly short half-life in plasma. Because these classical inhibitors are cleared slowly from tissues because of polyglutamation, they are often cytotoxic and are used in an infrequent short-infusion, eg. about 15 min, dosing regimen at high dosages.

Plevitrexed is a "non-classical" TS inhibitor in that it is not polyglutamated and is has the following properties: the RFC is the main transporter into cells; it is not a substrate for FPGS; TS Ki~0.4 nM, i.e. similar to polyglutamates of raltitexed and pemetrexed; it is readily effluxed from cells and thus not retained well in tissues/tumours; and has a long plasma half life.

Whilst pemetrexed has been approved for use in non-small cell lung cancer and pleural mesothelioma, it has also been proposed as a treatment for platinum-resistant ovarian cancer. For example in this indication 500 mg/m$^2$ pemetrexed was given on day 1 and gemcitabine on day 8 of a 21 day cycle (Clin Transl. Oncol (2009) 11:35-40 and at 900 mg/m$^2$ once every 21 days (J. Clin Oncol 27: 2686-2691). Further discussion of these trials and others is provided in Expert Opin. Investig. Drugs (2012) 21(4) and Expert Opin. Investig. Drugs (2013) 22((9) the latter of which notes a recommended single agent pemetrexed dose of 600 mg/m$^2$. This paper also notes that at that date no antifolate drug, which TS inhibitors are, had been approved for the treatment of ovarian cancer.

A further subset of this group of TS inhibitor compounds are FR-α targeted cyclopenta[g]quinazolines, described in patent applications WO-A-94/11354, WO-A-95/30673 and WO-A-03/020748. U.S. Pat. Nos. 5,789,417, 5,747,499, 7,250,511, 7,297,701, 7,528,141, 7,705,006, 7,863,284, 8,063,056, 8,486,955 and 8,552,016 are incorporated herein by reference for purposes of US patent rights. These documents teach that these compounds be administered at a dose within a range of 50-25000, particularly 50-5000, mg per square metre body area patient (mg/m$^2$), i.e. approximately 1500 mg/m$^2$, particularly 1-100 mg/kg. Higher dosages are taught could be employed and where subcutaneous infusion is used that the dose range may be increased to 1-1000 mg/kg, preferably 10-250 mg/kg, particularly 30-150 mg/kg.

These inhibitors may also be used against other cells expressing FR-β, in contrast to FR-α, particularly those involved in rheumatoid arthritis and acute myeloid leukemia. For this purpose U.S. Pat. No. 8,466,111 teaches a dose within the range 50-25000 mg/m$^2$, but also lists 5-25000 mg/m$^2$ but states that for subcutaneous administration the dose is increased to 1-1000 mg/kg or 0.1-10 mg/kg. There is discussion of topical administration at 0.1 to 10 mg/kg and oral tablets containing 1, 10, 50 and 100 mg of compound are disclosed as is an injection solution of 1, 10 and 50 mg/ml.

The higher dosages used are consistent with raltitrexed and pemetrexed and this subset of TS inhibitor compounds share similar properties such as: FR is the main transporter; uptake via FR is slower and more easily saturable than is RFC-mediated uptake of other antifolates; they are not a substrate for FPGS; and TS Ki~1.4 nM, which is similar to polyglutamates of raltitexed and pemetrexed. But because the compounds are readily effluxed from cells not retained in tissues/tumours, it was taught that high dosages should be tolerable.

Typically, TS requires inhibition for at least 24 hours to induce antiproliferative effects, and adequate intracellular exposure to drug of at least 2 to 3 days repeated frequently e.g. weekly for TS inhibitors to be effective. This is achieved by polyglutamation of raltitrexed and pemetrexed which overcomes the short plasma half-life and short extracellular exposure. Long intracellular exposure with plevitrexed, for example, is achieved by the unusually long plasma final half-life providing prolonged extracellular exposure.

Surprisingly on administration of the lead compound of this newer class FR-α targeted TS inhibitors to man half life levels were found to be unusually long. This compound, ONX-0801 (hereafter BTG945) has a high affinity for the alpha-folate receptor (FR-α) and enters cells via FR-α mediated transport. It has a modified glutamate ligand, L-glu-γ-D-glu dipeptide, and so is not a substrate for FPGS. It binds the α-FR with an affinity that is 70% of folic acid (FA) (Theti et al., 2003); it binds FR-β with similar affinity (van der Heijden et al., 2009) and it appears to have negligible affinity for the ubiquitous reduced folate carrier (RFC) except at high concentrations (Gibbs et al., 2005). This, it has been found, leads to a targeted concentration and time-dependent inhibition of tumour cell proliferation in vitro.

Once inside the cell, BTG945 binds irreversibly to the active site of thymidylate synthase, which is then prevented from performing its normal role in generating thymidine monophosphate (dTMP), a key step in DNA synthesis and repair similarly exploited by the approved TS-inhibitors.

A first in human Phase I clinical trial of BTG945, identified therein as ONX801, was initiated 30 Sep. 2009 with trial registration number ISRCCTN79302332 with the aim of finding a tolerable dose for 3 hour infusion on days 1, 8 and 15 of a 21 day cycle which would inhibit tumour cell growth. However, this trial was abandoned 30 Mar. 2011 due to toxicity at the predicted therapeutically effective dose of 45 mg/m$^2$ with incidence of Brochiolitis Obliterans with Organising Pneumonia (BOOP), irreversible and believed to increase with cumulative dose. This lead to the conclusion that the drug could not be used at the preconceived dose and regimen as this toxic dose was less than that taught as preferred minimal dose for treatment.

Given the high unmet need for the target treatment cohort, the present inventor has reassessed the dosage regimen that might be applied to the drug BTG945 to render it clinically useful. Analysis of unpublished human plasma drug levels suggested that much lower doses of drug would be necessary to avoid toxicity. The inventor and applicant initiated a new Phase I trial, EudraCT3941, at these presumed safe but predicted non-therapeutic doses wherein it has now been found that unexpected efficacy against platinum resistant tumours, particularly FR-α expressing tumours, in human patients is provided at far lower levels of drug than had previously been thought necessary and without occurrence of the treatment limiting BOOP. This efficacy has been exhibited as partial responses, using RECIST criteria, and stable disease, providing periods of progression free survival, particularly providing partial responses and/or objective response rates (ORR) in high percentages of ovarian cancer patients showing α-folate receptor expression, particularly when such expression exhibits receptor on tumour membranes.

So, whilst BTG945 has comparable Ki to raltitrexed and pemetrexed against isolated target thymidine synthase (1.2 nM as compared to 1.4 nM), the doses required to have efficacy in man are considerably less than those previously envisioned yet in the FR-α expressing preferred target group the compound appears to have efficacy far superior to that seen with other members of the TS inhibitor class.

Particularly surprising and advantageous is the finding that the side effect profile of BTG945 is unusually favourable. Dose limiting effects other than BOOP were not seen and BOOP itself has proven manageable and/or may be eliminated by optimised regimens using for example 2 or 3 weekly dosing. Side effects such as neutropenia, diarrhoea and hair loss, normally associated with thymidine synthase inhibitors, were not observed, nor were side effects associated with α-folate receptor antibody conjugates, such as diarrhoea, blurred vision and nausea. Furthermore conventional toxicities associated with cytotoxic chemotherapy, such as myelotoxicity, nephrotoxicity and neurotoxicity, were not observed.

Some trial patients' cancers were shown to respond at as low as 1 mg/m$^2$ in the treatment regimen outlined below. Side effects determined to date suggest that this regimen may be employed as monotherapy or in combination with any of the currently employed therapies described herein as toxicities are not overlapping. Such findings in the clinical setting now provide treatment of platinum resistant cancer that can be used as monotherapy or in combination with other available treatments with promise of extending PFS in a patient group with remaining high unmet need. Combination of the present treatment with first line treatments such as paclitaxel or carboplatin particularly are made available.

In a first aspect the present invention provides a compound of formula I

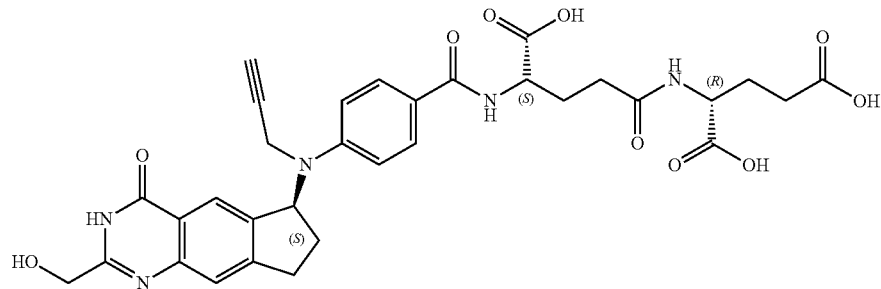

or a pharmaceutically acceptable salt or ester thereof for the treatment of cancer wherein
  (i) the cancer is one that has the characteristic of being a type prone to being or becoming refractory or resistant to platinum drug based therapy and
  (ii) the treatment is with a dose of between 1 mg/m$^2$ and 30 mg/m$^2$ of compound per patient body surface area per administration.

The treatment is preferably with a dosage regimen that results in plasma concentration of drug 0.5 µM or greater for at least 72 hours. More preferably the dosage regimen results in a plasma concentration of drug immediately after dosing that is from 1 µM to 5 µM for no more than 72 hours, preferably for no more than 60 hours. Most preferably the dosage regimen maintains the plasma concentration of drug from 0.1 µM to 2 µM for at least 50% of the treatment cycle period.

The treatment is preferably with a dosage regimen selected from
  a dose of 1 to 10 mg/m$^2$ administered in a 28 day cycle at 7 day intervals on day 1, 8, 15 and 22.
  a dose of 6 to 14 mg/m$^2$ administered in a 28 day cycle at 14 day intervals on day 1 and 15
  a dose of 10 to 30 mg/m$^2$ administered in a 21 day cycle on day 1.

The cancer is preferably one that is platinum refractory or resistant. Preferably the cancer is selected from ovarian, endometrial, mesothelial, non-small cell lung or a cancer derived from one of those.

More preferably the cancer is selected from those expressing α-folate receptors (FR-α) and especially those showing higher than background non-cancerous tissue levels of α-folate receptors. Most preferably the FR-α is expressed on the surface membranes of the cancer cells. Most preferably the cancer is an ovarian cancer such as epithelial ovarian, fallopian tube or peritoneal cancer, but may also be breast or lung cancer, for example triple negative breast or non-small cell lung. Specifically preferred cancer to be treated is serous ovarian cancer such as High-Grade Serous Ovarian Cancer (HGSOC) such as found in the salvage setting.

For the avoidance of doubt, platinum drug based therapy includes, but is not limited to, that with drugs Cis-platin or Carboplatin.

Whilst treatment with doses from 1 mg/m$^2$ to 30 mg/m$^2$ is included in the scope of the invention, preferred doses are from 3 mg/m$^2$ to 30 mg/m$^2$ of compound per patient body surface area per administration, more preferably doses of 5 mg/m$^2$ to 20 mg/m$^2$ of compound per patient body surface area per administration, still more preferably 8 mg/m$^2$ to 15 mg/m$^2$, most preferably 10 mg/m$^2$ to 15 mg/m$^2$ and particularly about 12 mg/m$^2$, eg. 11.5 mg/m$^2$ to 12.5 mg/m$^2$ of compound per patient body surface area per administration.

The dose is preferably administered intraperitoneally (IP) or intravenously (IV). IP administration will allow dosing with less risk of systemic side effects, particularly those that would affect the lungs such as BOOP. Typically the dose is administered intravenously.

In one preferred embodiment of the invention the compound is administered intraperitoneally (IP) as an injection, particularly a single injection, in a suitably sized volume, for example from 1 ml to 10 ml, more preferably 2 ml to 6 ml containing an appropriate amount of compound to meet the mg/m$^2$ dosage requirement. Typical such doses will be 2, 3, 4 or 5 ml of solution. Typically being an aqueous solution which may be in saline or in water for injection. The compound here is the 'Drug Substance' and the 'Drug Product' is a vial with the appropriate volume for a single IP administration. In a further preferred embodiment, multiple IP injections are given each as from 1 ml to 10 ml, but more preferably 2 ml to 6 ml solution containing the appropriate mg of Drug Substance. Typical such doses will be 2, 3, 4 or 5 ml of solution. Each 'Drug Product' provides for single or multiple IP injections and the Drug Product is a vial containing the Drug Substance, for example being a glass vial, eg a clear glass vial, with a stopper and suitable fixing to maintain the stopper in place such as an aluminium crimp seal.

In a further preferred embodiment, the compound is conveniently administered by injecting the content of a vial provided by pharmaceutical company supplier into a sterile saline bag as part of a saline drip. Typically the 'Drug Product' is a sterile aqueous solution of the Drug Substance BTG945 as trisodium salt, preferably being the dihydrate in solid form. The Drug Product is contained for example in a Type 1 clear glass vial, with a stopper and aluminium crimp seal. The labelled strength of each vial includes for example a 2-mL solution containing the appropriate mg of the Drug Substance. Conveniently, the only excipient in the BTG945 trisodium salt Drug Product can be sterile water for injection. Other components conventional in pharmaceutical compositions may of course be provided.

Drug Product vials are typically stored at low temperature and they are thawed prior to use, then the desired aliquot is withdrawn from 1 or multiple stoppered vials using a sterile syringe. This aliquot is then directly added to an infusion bag for further dilution in 250 mL of 0.9% sterile saline (USP) for injection, whether IP or IV. Once diluted into infusion bags, the prepared solution should preferably be administered to patients at ambient temperature within 24 hours. Prior to administration, the vials and bags should be protected from light.

In one preferred embodiment for IP infusion the aliquot is directly added to an infusion bag for further dilution in 10 ml, 15 ml, 25 ml or 50 ml of 0.9% sterile saline (USP) for IP injection or infusion. Once diluted these bags are treated as previously described.

More particularly the invention treats with the said calculated dose by infusions, particularly intravenous infusions (IV) or as single or multiple injections, as set out above spaced between 10 and 28 days apart, more preferably between 10 and 21 days apart and most preferably at dosing interval of about 14 days or 21 days. Still more preferably, when administered IV, the invention treats with a cumulative maximum of 150 mg/m$^2$ of compound per patient body surface area over the course of all infusions. More preferably this limit also applies to IP dosaging. More preferably the maximum cumulative dose is 144 mg/m$^2$.

Treatment in accordance with the present invention provides the compound preferably in infusions 14 or 21 days apart in 21 or 28 day cycles, most preferably 28 day cycles of two infusions each cycle, one on day 1 and one on day 15. These cycles are preferably repeated until the maximum cumulative dose is reached. Infusions are preferably carried out over 0.5 to 3 hours. As the treatment may be effective using as little as 1 mg/m$^2$ it will be realised that infusion rates of 1 hour will be sufficient. Thus infusions may be carried out over 0.5 to 1 hour, over 1 hour, but fewer than 3 hours.

More preferred dosages for each administration, eg infusion, are 1 mg/m$^2$ to 20 mg/m$^2$, preferably 3 mg/m$^2$ to 20 mg/m$^2$, more preferably 6 mg/m$^2$ to 18 mg/m$^2$, still more preferably from 8 mg/m$^2$ to 16 mg/m$^2$, eg from 10 mg/m$^2$ to 15 mg/m$^2$ and from 10 mg/m$^2$ to 12 mg/m$^2$. The most preferred dose is about 12 mg/m$^2$. At a 12 mg/m$^2$ dose given in 28 day cycle once every 14 days it can be seen that the maximum cumulative recommended dose will be reached in just under 6 months. A further preferred dose is a 12 mg/m$^2$ dose given once every 21 days in 21 day cycles. Further dosing may considered if the attending clinician is monitoring for the irreversible BOOP or similar side effect. When patients show signs of BOOP, for example if there is evidence of accumulation of inflammatory cellular exudate (AICE) on CT scan, the dose of drug compound should be reduced. It may also be prudent to stop drug administration for a short period, eg. 2 or 4 weeks, and then recommence with a lower preferred dose. ACIE has been observed on radiological scans, and it has been found that the condition stopped development or was reduced by halting dosing at 12 mg/m$^2$ for 2 weeks and then recommencing at 6 mg/m$^2$ until the maximum cumulative dose of 144 mg/m$^2$ is achieved.

In a particularly preferred embodiment, the preferred dosage administered achieves a blood concentration of about 0.5 μM or greater of the compound for at least 72 hrs, preferably less than 2.0 μM and more preferably about 0.7 μM or greater is achieved for at least 36 hrs or even more preferably about 0.9 μM or greater is achieved for at least 24 hrs, more preferably also being less than about 1.5 μM. This level is particularly preferred for IV administration. It is preferred that blood plasma levels of drug do not remain over 1 µM for more than 72 hours. Most preferably the dosage regimen maintains the plasma concentration of drug from 0.1 to 2 µM for at least 50% of the treatment cycle period. More preferably 0.1 to 1 µM for 50% of said period.

One particularly preferred cohort of suitable cancers for the treatment of the invention are those of female patients with newly diagnosed, histologically confirmed, high risk advanced (FIGO stage III-IV) BRCA mutated high grade serous or high grade endometrioid ovarian cancer, primary peritoneal cancer and/or fallopian-tube cancer.

Stage III patients preferably have had one attempt at optimal debulking surgery (upfront or interval debulking). Stage IV patients preferably have had either a biopsy and/or upfront or interval debulking surgery.

Particularly preferred are cancers of patients who have completed first line platinum (e.g. carboplatin or cisplatin) therapy (intravenous or intraperitoneal).

Most effectively treated by the present treatment are cancers that express α-folate receptors, particularly those expressing α-folate receptors on the membranes and/or in cytoplasm of at least 25% of cells of the cancer. More effectively treated are cancers that express α-folate receptors on or in at least 50% of the cells of the cancer and most effectively those expressing α-folate receptors on or in at least 75% of the cells of the cancer. Such levels may be determined by histological investigation of biopsy tissue using α-folate specific antibodies linked to visualisation agents as known in the art. For maximal efficacy the cancers are those that express FR-α on the cell membranes.

An example of a method for assessing α-folate receptor expression on membranes and in cyctoplasm is described in Kurosaki et al (2016) Int. J. Cancer: 138, 1994-2002 VC 2015 UICC where the tumour FR-α expression on FFPE (formalin-fixed paraffin-embedded) specimens was investigated using a specific antibody NCL-L-FRalpha (clone BN3.2; Leica Biosystems, UK) on a total of 164 EOCs, including borderline malignancies. Immunohistochemical staining was performed on full section slides using a BenchMark XT automated slide stainer and an iView DAB detection kit according to the manufacturer's instructions (Ventana Medical Systems, Tucson, AZ). Sections were deparaffinized, hydrated and antigen retrieval with Cell Conditioning Solution 1 (Ventana Medical Systems), followed by the mouse monoclonal anti-FRA antibody (1:40 dilution) incubation for 30 min. Positive staining was defined as the presence of membranous or membranous with cytoplasmic stain in tumor cells. Slides were scored as <1% positive tumor cells staining as negative, 1-25% positive tumor cells staining as weak (11), 25-75% staining as moderate (21) and greater than 75% staining as strong (31). The scoring of FR-α staining was evaluated in a blinded fashion by two independent observers. Any discrepancies were resolved by joint review over a double-headed microscope.

An alternative method for non-invasively ascertaining the suitability of a patient for treatment using the present invention assays for α-folate receptors in the blood. Such assays are described for example Basal et al (2009) PLOS ONE 4(7): e6292. Doi:10.1371/journal.pone.0006292, at least for ovarian cancers. Where α-folate receptor is found on membranes, it can be shed into circulating physiological fluids such as blood serum. In the case of ovarian cancer that team have found that patients with ovarian cancer have elevated levels of circulating α-folate receptor (FRα). This was found to be the case even where the cancer was in its early stages.

Kurosaki et al (2016) Int. J. Cancer: 138, 1994-2002 further confirm the applicability of serum α-folate receptor levels for diagnosing ovarian cancers of epithelial origin and correlated high serum FR-α with shorter PFS.

In addition to the ovarian tissue derived cancers specified above, FR-α overexpressing cancers that are suitable for treatment by the method and regimens of the invention also include cancers of the uterus, mesothelium, kidney, stomach, lung, colon, choroid plexus and brain. The highest levels of overexpression have been detected in non-mucinous ovarian cancer (Toffoli et al., 1998) where >90% of patients' tumours exhibit overexpression of the FR-α, but high levels have also been demonstrated in papillary serous endometrial cancer (Allard et al., 2007) renal cell cancer, and NSCLC (Parker et al., 2005). In addition, breast, primary CNS, colon and gastric cancers show varying degrees of expression (Low and Kularatne, 2009).

| Tumour Type | % tumours overexpressing FR-α |
|---|---|
| Ovary | 92% |
| Uterus | 91% |
| Mesothelium | 70% |
| Kidney | 50% |
| Stomach | 38% |
| Lung | 33% |
| Colon | 22% |
| Choroid plexus | 80% (ependymal) |
| Brain | 80% (metastases) |

Table 1: Alpha-Folate Receptor Expression in Selected Tumours (Weitman 1994; Garin-Chesa 1993; Bueno 2001)

The compound for use in the present invention has IUPAC nomenclature N—{N-{4-[N-((6S)-2-Hydroxymethyl-4-oxo-3,4,7,8-tetrahydro-6H-cyclo-penta[g]quinazolin-6-yl)-N-(prop-2-ynyl)amino]benzoyl}-L-γ-glutamyl}-D-glutamic acid or is a salt thereof and is herein referred to as BTG945, of which the trisodium salt thereof has the general formula II

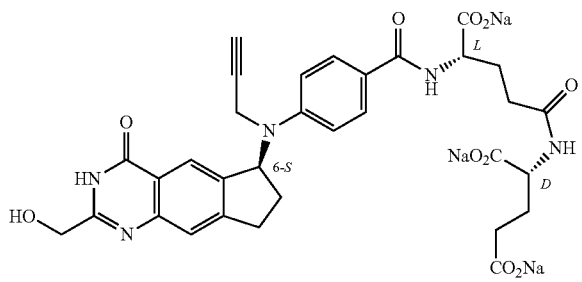

Alternate nomenclature is D-glutamic acid, N-[4-[2-propyn-1-yl-[(6S)-4,6,7,8-tetrahydro-2-(hydroxymethyl)-4-oxo-3H-cyclopenta[g]quinazolin-6-yl]amino]benzoyl]-L-gamma-glutamyl-, sodium salt.

The (6RS) racemate is also known to be an active form containing the active (6S) as described. It will be realised that doses may need to be at the higher end of the described ranges if they use the racemate as it contains only 50% of the (6S) form.

Where the compound is provided as an ester, this may be of a simple alcohol conjugated with one or more of the carboxylate moieties, which otherwise would be sites of sodium linkage in the formula above. The resulting alkyl esters may be any of those equivalent to the parent compound for regulatory purposes. A suitable pharmaceutically-acceptable ester form of the cyclopenta[g]quinazoline for the treatment of the invention is, for example, an ester with an aliphatic alcohol of up to 6 carbon atoms, for example a methyl, ethyl or tert-butyl ester. As three carboxy groups are present a salt or ester may be mono-acid-di-salt or -ester, di-acid-mono-salt or -ester or even tri-salt or -ester may be used.

A suitable pharmaceutically-acceptable salt form of the compound for the treatment of the invention is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra(2-hydroxyethyl)ammonium, salt. Most preferred is the trisodium salt.

The cyclopenta[g]quinazoline or salt described in the treatment of the present invention are believed in part at least to function as anti-cancer agents due to its ability to inhibit the enzyme thymidylate synthase.

The cyclopenta[g]quinazoline or salt composition may be in a form suitable for oral use, for example a tablet, capsule, aqueous or oily solution, suspension or emulsion; a form suitable for topical use, for example a cream, ointment, gel or aqueous or oily solution or suspension; a form suitable for nasal use, for example a snuff, nasal spray or nasal drops; a form suitable for vaginal or rectal use, for example a suppository; a form suitable for administration by inhalation, for example as a finely divided powder such as a dry powder, a microcrystalline form or a liquid aerosol; a form suitable for sub-lingual or buccal use, for example a tablet or capsule; or a form suitable for parenteral use (including intravenous, subcutaneous, intramuscular, intravascular or infusion use), for example a sterile aqueous or oily solution, emulsion or suspension. In general the above compositions may be prepared in a conventional manner using conventional excipients.

inhibiting agents or signal transduction inhibitors or other inhibitors of deregulated pathways in tumours.

However, those skilled in the art will realise that more conventionally, such combinations are administered separately but coordinated in time with treatment visits to the site of administration.

Particular regimens that are preferred to be employed with the compound for treatment of cancer of the first aspect of the invention are with one or more further anticancer agents selected from Cisplatin, Carboplatin, Doxorubicin, Bevacizumab Gemcitabine, Topetecan, Paclitaxel, Docetaxel, Etoposide, Nanoparticle albumin-bound paclitaxel, Lynparza (olaparib), Rubraca (rucaparib), Zejula (niraparib). Tecentriq (atezoizumab), Bavercio (avelumab)

Multiple combinations may also include bevacizumab in combination with paclitaxel, PEGylated liposomal doxorubicin, or topotecan. Further such examples of combinations are exemplified in the examples below.

Particularly advantageously the first aspect of the present invention employs doses of these combined drugs that are lower than those presently prescribed. This is particularly because there has been found not to be cross resistance to BTG945 with that to these other drugs and desired toxic effects on target cancer cells will often be cumulative. Thus in addition to exemplary dosage regimens provided in the examples herein, lower doses or less frequent doses of additional drugs may be exployed.

In a second aspect the present invention provides a method for treating a patient suffering from a cancer that has the characteristic of being a type prone to being or becoming refractory or resistant to platinum drug based therapy and wherein the treatment is with a dose of between 1 mg/m$^2$ and 30 mg/m$^2$ of compound per patient body surface area per administration of a compound of formula I

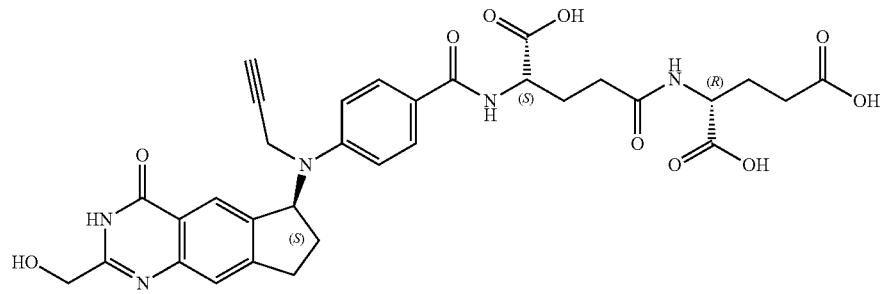

The preferred form of compound is for parenteral administration. Particularly preferred is compound for infusion, where the compound is preferably formulated with saline or water for injection. Alternatively it is provided in solid format ready to be admixed with said water or saline. For example the dihydrate of the trisodium salt.

The composition may contain, in addition to the cyclopenta[g]quinazoline used in the invention, one or more other anti-cancer substances or palliative substances selected from, for example, other antimetabolites, DNA interacting agents, immune-oncological agents, tumour blood vessel or a pharmaceutically acceptable salt or ester thereof for the treatment of cancer.

The cancer to be treated is as described above for the first aspect of the invention. The method preferably treats by administering the compound, salt or ester intraperitoneally (IP) or intravenously (IV).

The treatment is preferably with a dosage regimen that results in plasma concentration of drug of 0.5M or greater for at least 72 hours. More preferably the dosage regimen results in a plasma concentration of drug immediately after dosing that is from 1 to 5 µM for no more than 72 hours, preferably for no more than 60 hours. Most preferably the dosage regimen maintains the plasma concentration of drug of 0.1 to 2 μM for at least 50% of the treatment cycle period.

The treatment is preferably with a dosage regimen selected from
- a dose of from 1 to 10 mg/m² administered in a 28 day cycle at 7 day intervals on day 1, 8, 15 and 22.
- A dose of from 6 to 14 mg/m² administered in a 28 day cycle at 14 day intervals on day 1 and 15
- A dose of from 10 to 30 mg/m² administered in a 21 day cycle on day 1.

Whilst treatment with doses from 1 mg/m² to 30 mg/m² is included in the scope of the invention, preferred doses are from 3 mg/m² to 30 mg/m² of compound per patient body surface area per administration, more preferably doses of 5 mg/m² to 20 mg/m² of compound per patient body surface area per administration, still more preferably doses of 6 mg/m² to 18 mg/m² of compound per patient body surface area per administration, yet more preferably a dose of 8 mg/m² to 15 mg/m², most preferably 10 mg/m² to 15 mg/m² and particularly about 12 mg/m², eg. 11.5 mg/m² to 12.5 mg/m² of compound per patient body surface area per administration.

More preferably and particularly the method treats by infusions of the dose spaced between 10 and 28 days apart, more preferably between 10 and 21 days apart and most preferably at dosing interval of about 14 days or 21 days. Still more preferably, when administered IV, the invention treats with a cumulative maximum of 150 mg/m² of compound per patient body surface area taking into account all of the infusions. More preferably this limit also applies to IP dosing. More preferably the maximum cumulative dose is 144 mg/m².

The method in accordance with the present invention provides the compound preferably as infusions 14 or 21 days apart in 21 or 28 day cycles, most preferably 28 days. These cycles are preferably repeated until the maximum cumulative dose is reached. Infusions are preferably carried out over 0.5 to 3 hours. Infusions can be carried out over 0.5 to 1 hour, over 1 hour or from to 1 to fewer than 3 hours. As the treatment may be effective using as little as 1 mg/m² or 3 mg/m² it will be realised that infusion rates of 1 hour will be sufficient.

More preferred dosages for each infusion are 1 mg/m² to 20 mg/m², more preferably from 10 mg/m² to 15 mg/m².

The most preferred dose is about 12 mg/m². At a 12 mg/m² dose given once every 14 days in 28 day cycles it can be seen that the maximum cumulative recommended dose will be reached in just under 6 months. This is composed of 12 infusions of 12 mg/m² of compound providing cumulative total 144 mg/m². A further preferred dosing schedule is a 12 mg/m² dose given once every 21 days in 21 day cycles. Further dosing may considered preferably only if the attending clinician is monitoring for the irreversible BOOP or similar side effect.

The method of the second aspect of the present invention further provides for treatment with the compound of the formula I in combination with a therapeutically effective amount of one or more further anticancer agents.

The one or more further anticancer agents used in this combination therapy are preferably selected from Cisplatin, Carboplatin, Doxorubicin, Bevacizumab Gemcitabine, Topetecan, Paclitaxel, Docetaxel, Etoposide, Nanoparticle albumin-bound paclitaxel, Lynparza (olaparib), Rubraca (rucaparib), Zejula (niraparib). Tecentriq (atezoizumab), Bavercio (avelumab) and Keytruda (pembrolizumab).

Multiple combinations may also include bevacizumab in combination with paclitaxel, pegylated liposomal doxorubicin, or topotecan. Further such examples of combinations are exemplified in the examples below.

Preferred combinations are with paclitaxel or carboplatin or both.

Given the nature of the side effects seen in lung in the failed trial, the inventor also contemplates that the dosage regimen of the invention may also incorporate administration of a steroid to alleviate inflammation of the lung.

A third aspect of the present invention provides a method for treating a patient suffering from a cancer that has the characteristic of being a type prone to being or becoming refractory or resistant to platinum drug based therapy and wherein the treatment is with a dose of between 1 mg/m² and 30 mg/m² of compound per patient body surface area per administration of a compound of formula I

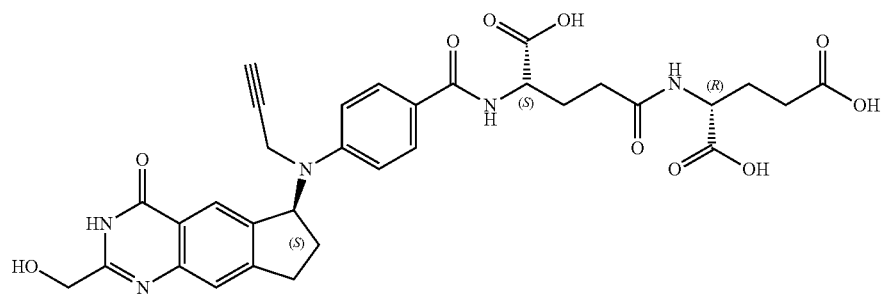

or a pharmaceutically acceptable salt or ester thereof in combination with an anti-inflammatory corticosteroid. Preferred corticosteroids are selected from the group consisting of prednisone, methylprednisolone, dexamethasone and prednisolone and hydrocortisone.

In a fourth aspect the present invention provides novel dosage forms of the compound of formula I

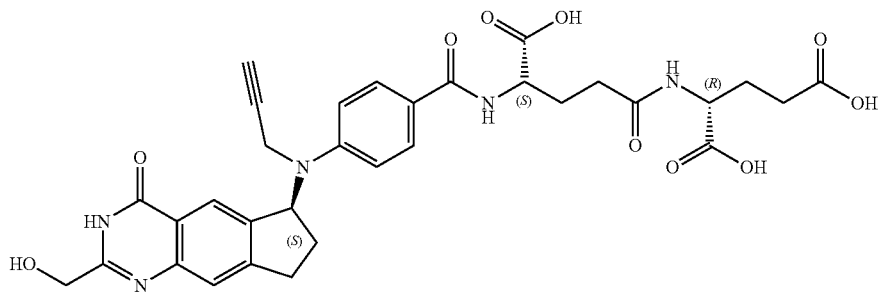

comprising a single dosage unit containing said compound or a pharmaceutically acceptable salt or ester thereof characterised in that the amount of said compound in the dosage unit is between 0.5 mg and 40 mg.

More preferably the dosage unit of the invention contains between 1mg and 30 mg of the compound of formula I or salt or ester thereof. Still more preferably the dosage unit contains between 5 mg and 26 mg of the compound of formula I. Most preferably the dosage unit contains between 10 mg and 24 mg of the compound or salt or ester of formula I.

The preferred dosage form will be a container of the compound of formula I or its salt or ester, more preferably the sodium salt, as a sterile solid or aqueous solution in a medium such as water for injection or saline. The sterile solid is preferably BTG945 or a salt or ester thereof free of other materials. Such container would be such that the liquid contained therein, or added thereto when a solid format is provided, could be taken up into a syringe in an amount suited to the body surface area of the patient such as to transfer the required dose of 1 mg/m$^2$ to 30 mg/m$^2$.

Preferably the dose is provided as an aqueous solution in a vial. Such a dosage form or formulation will preferably be a vial containing from 1 ml to 30 mls of aqueous solution of the compound for treatment, more preferably from 1 ml to 20 ml, still more preferably from 1 ml to 10 ml and most preferably between 2 ml and 6 ml. Alternatively the dose is provided as solid form of the compound for treatment without liquid. Thus a preferred vial of the invention will contain from 0.5 mg to 40 mg of compound in 1 ml to 30 ml of aqueous solution, still more preferably 5 mg to 26 mg in 1 ml to 20 ml of aqueous solution and most preferably 10 mg to 24 mg in 1 ml to 10 ml of aqueous solution, eg about 6 mg or 12 mg in 2 ml to 6 ml of aqueous solution.

It will be realised by those skilled in the art that pharmaceuticals are expensive commodities and that it is desirable not to waste compound not required for a given treatment. As BTG945 is potentially toxic above the now taught doses it would be inappropriate for more than required to be provided in the clinical setting. Thus as a preferred dose per patient surface area is 6 mg/m$^2$ or 12 mg/m$^2$ and patients typically have surface area between 1 m$^2$ and 2.5 m$^2$ in developed countries, with patients with unusually high BMI often capped at 2 m$^2$, it can be seen that a novel preferred useable vial content, whether in dried solid or solution form, would be between 6 mg to 24 mg drug compound more preferred between 10 mg and 24 mg drug compound. Thus vials of drug content 6 mg, 8 mg, 10 mg, 12 mg, 14 mg, 16 mg, 18 mg, 20 mg and 24 mg are disclosed as novel embodiments of the invention. Particularly those where drug is in the form of dried BTG945 salt and/or its dehydrate, or its simple solution in water or saline for injection.

The compound for the treatment of the invention may be synthesised as described in the aforementioned patent applications or as set out in more recent patent U.S. Pat. No. 8,809,526 (Onyx) and patent application US2013/0345423 (Onyx).

FIGURES

FIGS. 1 to 5 show the clinical results of trial with the treatment of the present invention in humans.

FIG. 1: Shows the % change in tumours using RECIST criteria in patients in the dose escalation phase of the trial of Example 1 Weekly schedule is indicated by asterisk and an α-folate expressing tumour indicated by a cross.

Figure 2:
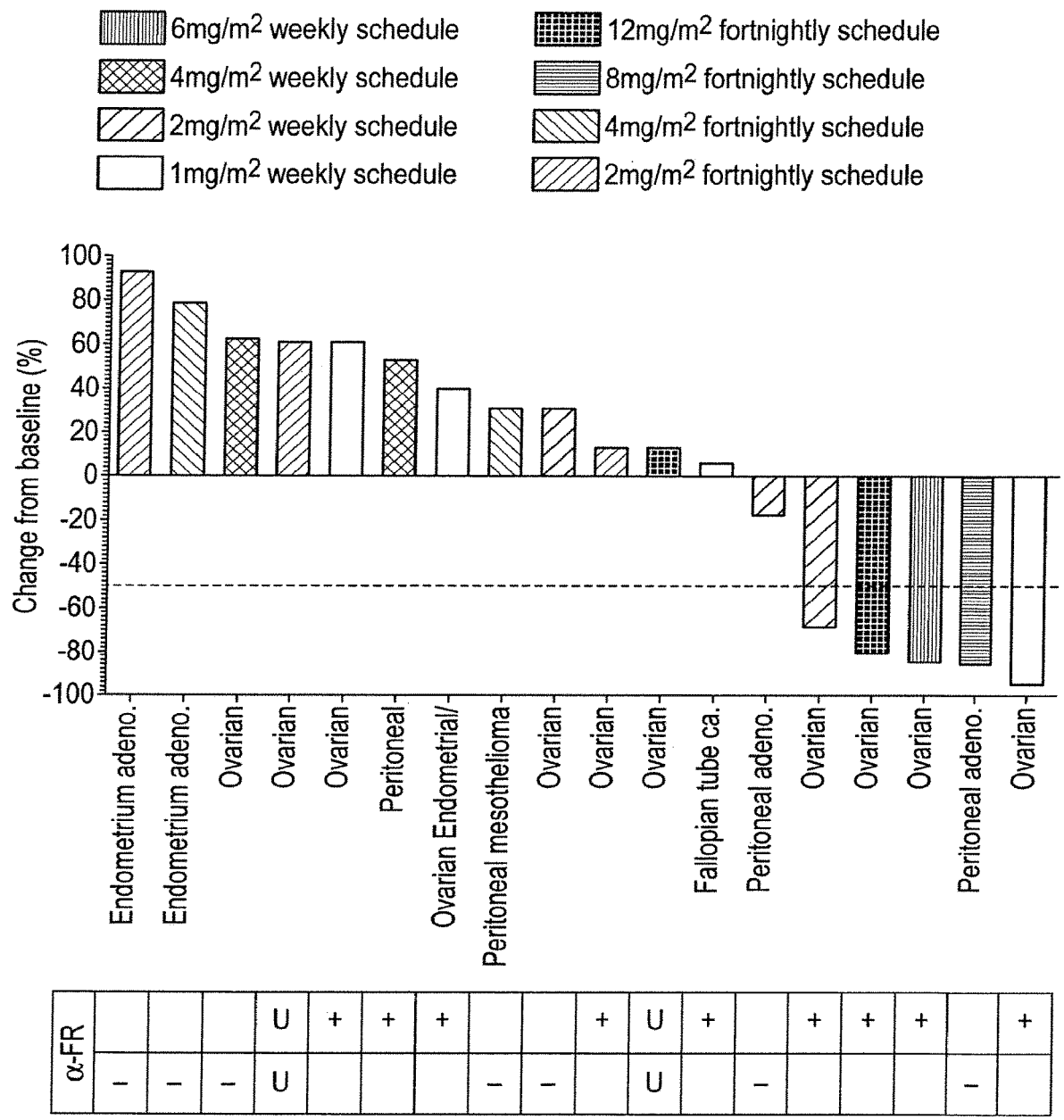

FIG. 2: Shows the % change in tumours as measured by CA125 level in escalation phase of the trial of example 1. Numbers represent dose mg/m$^2$ and letters whether weekly (w) or fortnightly (f) and an α-folate expressing tumour indicated by a cross.

Figure 3:
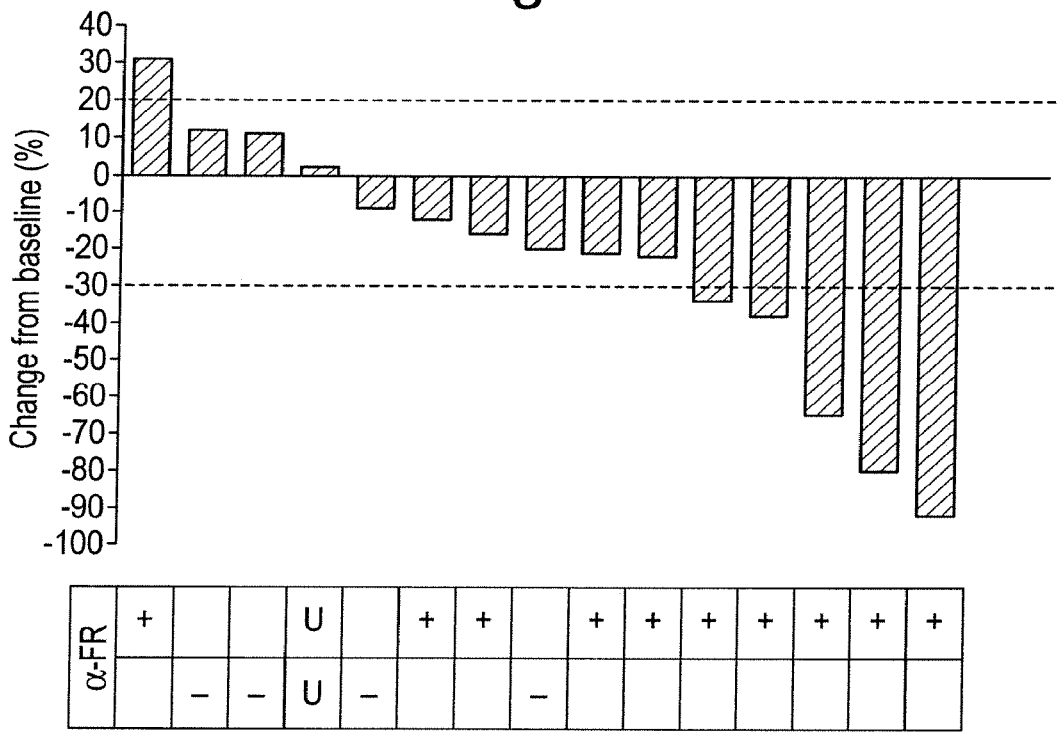

FIG. 3: Shows the % change in tumours using RECIST criteria in patients in the expansion phase of the trial of Example 1 using 12 mg/m$^2$ dose once every 14 days in 28 day cycles. An α-folate expressing tumour is indicated by a cross.

Figure 4:
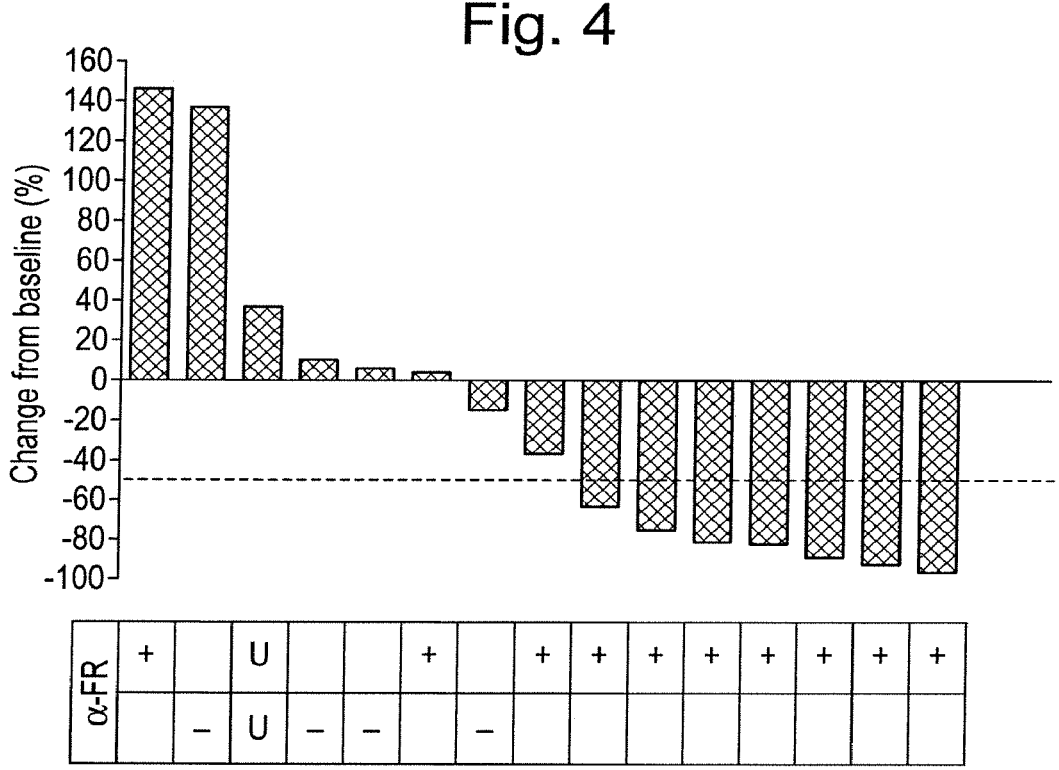

FIG. 4: Shows the % change in tumours as measured using CA125 level in patients in the expansion phase of the trial of Example 1 using 12 mg/m$^2$ dose once every 14 days in 28 day cycles. An α-folate expressing tumour is indicated by a cross.

Figure 5:
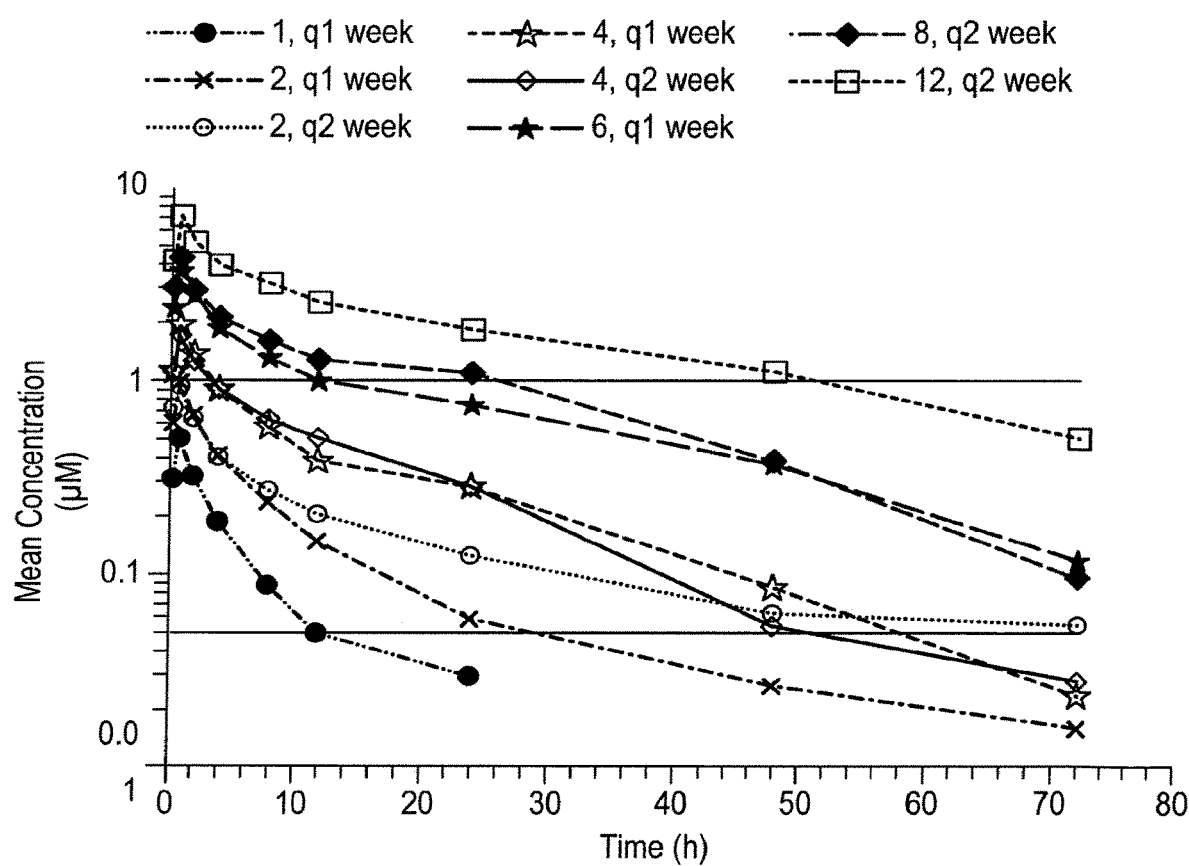

FIG. 5: Shows the mean blood concentration (μM) of compound ONX-0801/BTG 945 versus time (hours) for patients under different dose regimens in the escalation phase of the trial before selection of the expansion dose.

EXAMPLES

The present invention will now be illustrated by the following non-limiting examples. Further embodiments will occur to those skilled in the art in the light of these.

Preferred target cancer to be treated with the following example regimens will be in patients with the following:
  Histologically confirmed epithelial ovarian, fallopian tube, or peritoneal cancer.
  Platinum resistant/refractory disease, defined as disease progression within 180 days following the last administered dose of platinum therapy (resistant), or lack of response or disease progression while receiving the most recent platinum based therapy (refractory), respectively.
  Received up to 3 lines of chemotherapy for platinum sensitive disease, most recently platinum containing, and no prior therapy for platinum resistant disease

Example 1: Treatment of Patients with 1 mg/m² to 12 mg/m² BTG 945 (Trisodium Salt Form Compound of Formula II) as Monotherapy Methods: A 3+3 dose escalation design was used and two IV schedules were explored. Schedule A, weekly dosing (QW) and schedule B, once every 2 weeks dosing (Q2W). A cycle consisted of 4 weeks and treatment was stopped after 6 cycles in both schedules. An expansion cohort to evaluate clinical activity in patients with FR-α overexpressing high grade serous ovarian cancer (HGSOC) was initiated.

Results: 21 patients each were treated in schedule A and B exploring doses ranging from 1-6 mg/m² and 2-12 mg/m², respectively. The dose limiting toxicity on schedule A was G3 cellulitis; no dose limiting toxicity was seen on schedule B. The most common toxicities were fatigue 15/42 (36%), nausea 9/42 (21%) and dysgeusia 5/42 (12%). Within schedule A at 4 mg/m², 2 patients developed suspected drug-related changes on pulmonary function tests (drop in Dlco>15%) at cycles 5 and 6, respectively. No cases of suspected drug-related drop in Dlco were noted in patients treated in schedule B. No grade 3-4 diarrhea, mucositis or neutropenia were seen in either cohort. The Cmax, AUC and half-life at 12 mg/m² were 4952 ng/ml, 85170 h*ng/ml and 26 h, respectively. Pre-clinical PK-PD modelling aimed to achieve concentrations between 0.05-1 µM and this was achieved for periods of 48 h at doses of 4 mg/m² and above.

Concentrations above 0.5 µM were achieved for 72 hours at doses above 6 mg/m². Evidence of thymidylate synthase inhibition was observed using FLT PET imaging See *Cancer Res* 68. 3827-3834. 2008 (Pillai et al).

Based on safety and PK, the recommended phase II dose (RP2D) of BTG945 (was ONX801) was 12 mg/m² Q2W and an expansion in patients with HGSOC was initiated. 5 patients with HGSOC had partial responses (PRs) in the dose escalation cohort. In the expansion cohort in patients with HGSOC, 5/11 patients had PRs to date of this filing. Archival samples have been analysed from 8/11 patients in the expansion cohort. 4/4 AFR+ve did have PR and 4/4 AFR−ve patients did not have a PR following treatment with BTG945, respectively. RECIST and CA125 responses are shown in FIGS. 1 to 4.

Conclusions: The RP2D of BTG945 is 12 mg/m² Q2W. At the RP2D, multiple patients with AFR overexpressing HGSOC have had PRs and further randomized biomarker prespecified phase II trials are warranted.

Example 2: Combination Therapy with BTG945 and Other Anti-Cancer Therapies 12 mg/m² BTG945 is administered IV in saline for injection on day 1 and day 15 of a 28 day cycle over 1 hour up to a maximum of 6 cycles. One or more of the following exemplary therapeutic regimes are administered in coordination with this treatment as follows:

Example 2.1 Liposomal doxorubicin 40-50 mg/m² IV over 30 min; every 21 d

Example 2.2 Gemcitabine 1000 mg/m² IV over 30 min on days 1 and 8; every 21 d

Example 2.3 Topotecan 1.25-1.5 mg/m² IV over 30 min on days 1-5; every 21 d

Example 2.4 Paclitaxel 80 mg/m² IV over 1 h weekly

Example 2.5 Docetaxel 75-100 mg/m² IV over 1 h q 21 days

Example 2.6 Etoposide 50 mg/m²/day PO for 21 days q 28 days

Example 2.7 Nanoparticle albumin-bound paclitaxel 100 mg/m 2 IV over 30 min given weekly (days 1, 8, and 15) q 28 days Example 2.8 Keytruda 200 mg iv q3 weeks with 945 at any line of chemotherapy.

Example 3: Combination Therapy with BTG945 and Other Anti-Cancer Therapies for Platinum Sensitive Cancers 12 mg/m² BTG945 is administered IV in saline for injection on day 1 and day 15 of a 28 day cycle over 1 hour up to a maximum of 6 cycles. One or more of the following exemplary therapeutic regimes are administered in coordination with this treatment as follows:

Example 3.1 Paclitaxel 135 mg/m² IV over 24 h on day 1 plus cisplatin 100 mg/m² IP on day 2 (may reduce dose to 75 mg/m²) plus paclitaxel 60 mg/m² IP on day 8 for six or more cycles, provided that the disease is responsive. The cisplatin dose may be reduced to 75 mg/m 2 IP on day 2; some clinicians give paclitaxel 135 mg/m² IV over 3 h followed by cisplatin 75 mg/m 2 IP, both on day 1 and on an outpatient basis Example 3.2 Carboplatin treatment. Normal range of carboplatin AUC for treatment of ovarian carcinoma is from 5 to 7.5; patients who have received extensive prior chemotherapy or radiation should start with an AUC<5

Example 4: Combination Therapy with BTG945 and Other Anti-Cancer Therapies for Platinum Sensitive Cancers where Patient Cannot Tolerate IP Administration 12 mg/m² BTG945 is administered IV in saline for injection on day 1 and day 15 of a 28 day cycle over 1 hour up to a maximum of 6 cycles. One or more of the following exemplary therapeutic regimes are administered in coordination with this treatment as follows:

Example 4.1 Paclitaxel 175 mg/m 2 IV over 3 h plus carboplatin AUC 7.5 IV over 1 h on day 1; every 21 d for six cycles or Example 4.2 Docetaxel 75 mg/m 2 IV over 1 h plus carboplatin AUC 5 IV over 1 h on day 1; every 21 d for six cycles

Example 5: Combination Therapy with BTG945 and Other Anti-Cancer Therapies for Platinum Sensitive Stage III and IV Platinum-Sensitive Recurrence Cancers Platinum-sensitive recurrence: If recurrence occurs >6 mo from initial or subsequent complete clinical response to platinum-containing chemotherapy, the patient should be treated with 12 mg/m² BTG945 administered IV in saline for injection on day 1 and day 15 of a 28 day cycle over 1 hour up to a maximum of 6 cycles together with one of the IV platinum-containing combination regimens below. The choice depends on factors such as preexisting comorbidity, prior toxicities, and physician and patient preference. Regimens are as follows:

Example 5.1 Carboplatin AUC 5 IV push plus liposomal doxorubicin 30 mg/m² IV over 30 min; every 28 d for six cycles Example 5.2 Paclitaxel 175 mg/m 2 IV over 3 h plus carboplatin AUC 5 (Calvert) IV over 1 h; every 21 d for six cycles Example 5.3 Paclitaxel 80 mg/m² IV over 1 h weekly days 1, 8, and 15 plus carboplatin AUC 6 IV over 1 h on day 1; every 21 days for six cycles Example 5.4 Docetaxel 75 mg/m² IV over 1 h plus carboplatin AUC 5 IV over 1 h; every 21 d for six cycles Example 5.5 Gemcitabine 1000 mg/m² IV over 30 min on days 1 and 8 plus carboplatin AUC 4 IV over 1 h on day 1; every 21 days for six cycles

Example 6: Combination Therapy with BTG945 and Other Anti-Cancer Therapies for Platinum Sensitive Stage III and IV Platinum-Sensitive Recurrence Cancers Consideration may be given to bevacizumab either alone or with carboplatin/gemcitabine but the use of this agent is still controversial. Platinum-sensitive recurrence: If recurrence occurs >6 mo from initial or subsequent complete clinical response to platinum-containing chemotherapy, the patient should be treated with 12 mg/m² BTG945 administered IV in saline for injection on day 1 and day 15 of a 28 day cycle over 1 hour up to a maximum of 6 cycles together with one of the IV platinum-containing combination regimens below.

Example 6.1 Bevacizumab 15 mg/kg IV (initially over 90 min, then over 60 min, and finally over 30 min for subsequent infusions); every 21 d until disease progression, irrespective of prior platinum response Example 6.2 Gemcitabine 1000 mg/m² IV over 30 min on days 1 and 8 plus carboplatin AUC 4 IV push on day 1; every 21 d for 6-10 cycles plus bevacizumab 15 mg/kg IV on day 1 prior to gemcitabine and carboplatin and continued until progression of disease or unacceptable toxicity Example 6.3 Bevacizumab 10 mg/kg IV every 14 d in combination with one of the following IV chemotherapy regimens: paclitaxel, pegylated liposomal doxorubicin, or topotecan (topotecan is given weekly)

Example 6.4 Bevacizumab 15 mg/kg IV every 21 d in combination with topotecan (every 21 d)

Example 6.5 Bevacizumab 15 mg/kg IV (initially over 90 min, then over 60 min, and finally over 30 min for subsequent infusions); every 21 d until progression Example 6.6 Bevacizumab 10 mg/kg IV on days 1 and 15 plus topotecan 4 mg/m 2 IV on days 1, 8, and 15, q 28 days

Example 7: Combination Therapy with BTG945 and Platinum-Sensitive or Resistant or Refractory BRCA-Mutated Stage III and IV Platinum-Sensitive Recurrence Cancers For patients diagnosed as BRCA-mutated (as detected by an FDA-approved test, BRACAnalysis CDxTM) in patients who have been treated with three or more prior lines of chemotherapy: 12 mg/m² BTG945 administered IV in saline for injection on day 1 and day 15 of a 28 day cycle over 1 hour up to a maximum of 6 cycles whilst Olaparib 400 mg is administered PO BID continuously In the European Union, olaparib 400 mg PO BID is approved as monotherapy for the maintenance treatment of adult patients with platinum-sensitive, relapsed, BRCA-mutated (germline and/or somatic) high-grade serous epithelial, fallopian tube, or primary peritoneal cancer who are showing response (complete or partial) to platinum-based chemotherapy.

The invention claimed is:

1. A method of treating cancer in a patient in need thereof comprising administering to the patient a compound of formula I or a pharmaceutically acceptable salt or ester thereof, wherein:
the cancer has the characteristic of being a type prone to being or becoming refractory or resistant to platinum drug based therapy,
the compound or pharmaceutically acceptable salt or ester thereof is administered to the patient at a dose of from 6 mg/m² to 14 mg/m² of compound or pharmaceutically acceptable salt or ester thereof per patient body surface area per administration, and
each of the administrations is in a 28-day cycle at 14-day intervals.

2. The method according to claim 1, wherein the administration is in a first dose on day 1 of the 28-day cycle and a second dose on day 15 of the 28-day cycle.

3. The method according to claim 1, further comprising administering a therapeutically effective amount of one or more further anticancer agents.

4. The method according to claim 2, further comprising administering a therapeutically effective amount of one or more further anticancer agents.

5. The method according to claim 1, further comprising administering a PARP inhibitor to the patient.

6. The method according to claim 1, wherein the PARP inhibitor is chosen from olaparib, rucaparib, and niraparib.

7. The method according to claim 2, further comprising administering a PARP inhibitor to the patient.

8. The method according to claim 2, wherein the PARP inhibitor is chosen from olaparib, rucaparib, and niraparib.

9. The method according to claim 1, wherein the cancer is chosen from cancers expressing a-folate receptors (FR-a).

10. The method according to claim 1, wherein the cancer is ovarian cancer.

11. The method according to claim 1, wherein the cancer is epithelial ovarian cancer, fallopian tube cancer, or peritoneal cancer.

12. The method according to claim 1, wherein the cancer is serous ovarian cancer.

13. The method according to claim 1, wherein the cancer is High-Grade Serous Ovarian Cancer (HGSOC).

14. The method according to claim 1, wherein the dose is administered intraperitoneally (IP) or intravenously (IV).

15. The method according to claim 1, wherein the administration is an infusion of from 11.5 mg/m² to 12.5 mg/m² per administration.

16. The method according to claim 1, wherein the administration is an infusion of about 12 mg/m² per administration.

17. The method according to claim 1, wherein the treatment is with a cumulative maximum of 150 mg/m² of compound or pharmaceutically acceptable salt or ester thereof per patient body surface area over the course of all the administrations.

18. The method according to claim 1, wherein the compound is the trisodium salt of formula II:

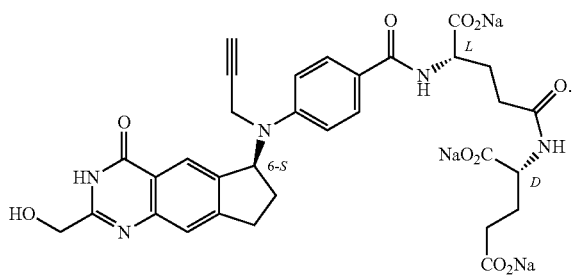

19. The method according to claim 18, further comprising administering a PARP inhibitor to the patient.

20. The method according to claim 19, wherein the PARP inhibitor is chosen from olaparib, rucaparib, and niraparib.

21. The method according to claim 19, wherein the trisodium salt of formula II and the PARP inhibitor are administered to the patient separately.

22. The method according to claim 20, wherein the trisodium salt of formula II and the PARP inhibitor chosen from olaparib, rucaparib, and niraparib are administered to the patient separately.

23. The method according to claim 18, wherein the treatment is with a cumulative maximum of 150 mg/m² of compound or pharmaceutically acceptable salt or ester thereof per patient body surface area over the course of all the administrations.

24. The method according to claim 1, wherein the administration is an infusion of from 8.5 mg/m² to 9.5 mg/m² per administration.

25. The method according to claim 1, wherein the administration is an infusion of about 9 mg/m² per administration.

\* \* \* \* \*